US006183741B1

(12) United States Patent
Rowlands et al.

(10) Patent No.: US 6,183,741 B1
(45) Date of Patent: Feb. 6, 2001

(54) METHOD FOR REDUCING INSOLUBLES IN A GELATIN SOLUTION

(75) Inventors: Anne G. Rowlands, Honeoye Falls, NY (US); Robert F. Rainville, North Andover, MA (US)

(73) Assignee: Eastman Kodak Company, Rochester, NY (US)

( * ) Notice: Under 35 U.S.C. 154(b), the term of this patent shall be extended for 0 days.

(21) Appl. No.: 09/183,149

(22) Filed: Oct. 30, 1998

(51) Int. Cl.[7] .................................................... A61K 38/47

(52) U.S. Cl. .................... 424/94.61; 424/94.6; 435/267; 435/272; 435/273; 435/202; 435/203; 435/204; 530/534

(58) Field of Search ............................... 424/94.61, 94.6, 424/543, 549, 548; 435/202, 203, 204, 267, 272, 273; 530/534

(56) References Cited

U.S. PATENT DOCUMENTS

| | | | | |
|---|---|---|---|---|
| 2,681,294 | * | 6/1954 | Beguin | 430/523 |
| 2,761,419 | * | 9/1956 | Mercier et al. | 118/412 |
| 2,761,791 | * | 9/1956 | Russell | 430/502 |
| 3,508,947 | * | 4/1970 | Hughes | 430/538 |
| 3,632,374 | * | 1/1972 | Greiller | 430/538 |
| 4,287,240 | * | 9/1981 | O'Connor | 427/402 |

* cited by examiner

*Primary Examiner*—Jean C. Witz
(74) *Attorney, Agent, or Firm*—Carl F. Ruoff; Doreen M. Wells

(57) ABSTRACT

The present invention is a process for reducing gelatin insolubles which includes providing a gelatin solution and adding to the gelatin solution amylase in an amount to provide a concentration of amylase of at least 0.1 ppm for a time sufficient to reduce gelatin insolubles. The present invention also provides a gelatin having a Bloom strength of from 60 to 400 and a concentration of amylase of greater than 0.1 ppm.

4 Claims, 1 Drawing Sheet

METHOD FOR REDUCING INSOLUBLES IN A GELATIN SOLUTION

FIELD OF THE INVENTION

The present invention relates to gelatin solutions and more particularly to the reduction of gelatin insolubles in gelatin solutions.

BACKGROUND OF THE INVENTION

In the coating of photographic layers on a support such as a film base or paper, a plurality of individual layers are often coated on the support simultaneously, with each successive layer being superimposed on the layer below by means of a coating hopper. One type of coating hopper, known as a multiple slide hopper, is comprised of individual slide elements which are separated by slots and cavities. By introducing each coating liquid into a cavity, the liquid stream is distributed to the desired width and then metered uniformly across the coating width by flowing through the narrow slot. Upon exiting the slot, the layer flows by gravity down the inclined slide surface. Layers of coating liquids then become superimposed on one another as layers from upstream slots flow over the layers exiting from the downstream slots. At the end of the slide surface, the liquid flows onto and coats the moving web. One method for continuously coating thin layers of a liquid composition on a moving substrate such as a continuous web is the so-called curtain coating method. An early description of a curtain-coating method and apparatus for use in the manufacture of photographic film and paper is found in the patent to Hughes, U.S. Pat. No. 3,508,947, incorporated herein by reference. This and subsequent patents relating to curtain coating (e.g., U.S. Pat. No. 3,632,374 and U.S. Pat. No. 4,287,240) describe the use of a coating hopper to form a free-falling curtain of liquid photographic coating composition which impinges transversely across a moving web of film or paper and forms a coated layer thereon.

Another method of coating liquid layers is bead coating, as disclosed, for example, in the patent to Beguin, U.S. Pat. No. 2,681,294, the patent to Mercier et al., U.S. Pat. No. 2, 761,419, the patent to Russell, U.S. Pat. No. 2,761,791 and others, is a valuable process and incorporated herein by reference.

In coated photographic products insoluble particulates from gelatin sources can cause physical coating defects in the liquid layers. The presence of physical coating defects results in product waste, or if undetected release of lower quality product. To prevent coating of insoluble particulates from gelatin sources, filtration is used at multiple stages in the manufacture of coated photographic products. In photographic products gelatin is a large component of photographic melts on a per weight basis. Therefore the concentration of gelatin insolubles (gel slugs) present in photographic gelatin can dramatically effect the frequency of physical coating defects. To date efforts to reduce the number of gel slugs in photographic gelatin have focused on reduction of gel slug formation during the gelatin manufacturing process and removal of gel slugs from gelatin solutions by filtration. Reduction of gel slug formation during gelatin manufacturing can be achieved to some degree through optimization of drying conditions, however to date no gelatin manufacturer has been able to completely eliminate gel slugs. Although filtration of gelatin solutions can reduce gel slug levels this method increases process cycle time and is costly due to filter changes.

An object of the present invention is to reduce gel slugs or gelatin insolubles in a gelatin solution.

Another object of the present invention is to provide a gelatin having reduced gelatin insolubles.

SUMMARY OF THE INVENTION

The present invention is a process for reducing gelatin insolubles which includes providing a gelatin solution and adding to the gelatin solution amylase in an amount to provide a concentration of amylase of at least 0.1 ppm for a time sufficient to reduce gelatin insolubles. The present invention also provides a gelatin having a Bloom strength of from 60 to 400 and a concentration of amylase of greater than 0.1ppm.

Figure 1:
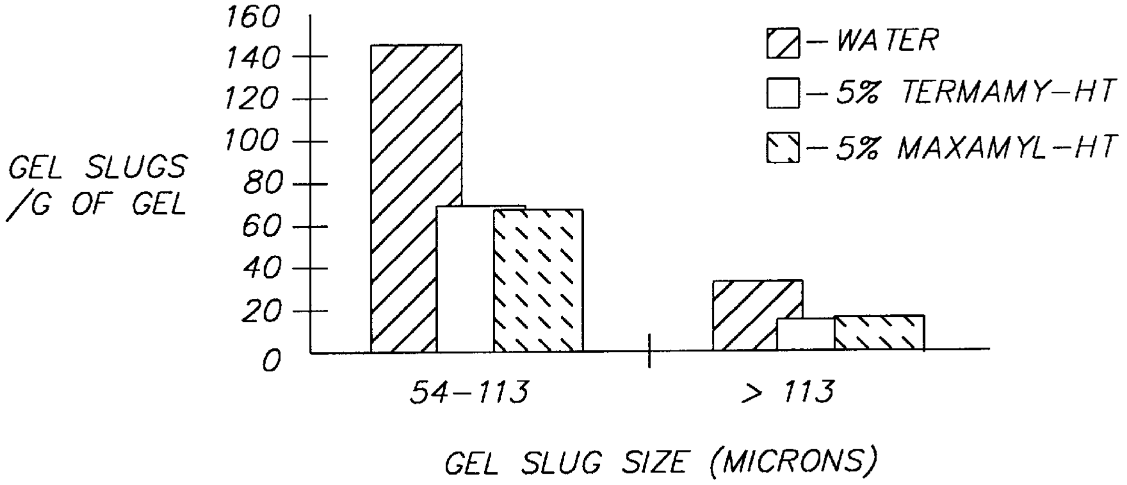
FIG. 1 shows the gel slug size versus gel slugs per gram of gelatin for gelatin solutions treated with and without amylase.

For a better understanding of the present invention, reference is made to the following detailed description in connection with the above described drawing.

DETAILED DESCRIPTION OF THE INVENTION

The present invention is a process for reducing gelatin insolubles in a gelatin solution. A gelatin containing solution is provided and added to an amylase solution at a concentration of at least 0.1ppm. The gelatin solution is treated for a time sufficient to remove gelatin insolubles.

Amylases are a group of widely occurring hydrolases which cleave the alpha 1,4-glyosidic bonds in oligosaccharides and polysaccharides like starch, glycogen and dextrans. Preferred conditions for amylase use vary by individual amylase as a function of the substrate and reaction conditions.

Amylase effectiveness on removal of gelatin insolubles was determined b)y providing, gelatin solutions incubated with amylase (protease free) for varied amounts of time at temperatures ranging from 40–55° C. Gelatin insolubles in treated and untreated gelatins were determined by analytical filtration followed by visualization with a protein specific dye. Numbers and sizes of gelatin insolubles were quantified by a computer interfaced automated visual imaging system. Briefly, a 5% gelatin solution was filtered through a 12 micron pore size nitrocellulose filter, rinsed with water, stained with Ponceau S dye and rinsed again with water. The resulting filter was dried and analyzed by an automated visual inspection system. Equipment used included a Wild Macroscope with RS-170 camera, Ludl 8"×8" X-Y stage, autofocus and color light box. Gelatin insolubles measured ranged from 20 to greater than 110 microns in diameter. Numbers of gelatin insolubles per a specified size range were reported per gram of gelatin (moisture corrected).

Amylases

Maxamyl L Genencor International

Termamyl 12L Type L Novo Nordisk

To maintain gelatin integrity amylase solutions used must be free of protease activity. The method used to remove protease activity has been described in U.S. Ser. No. 09/182, 936 (Docket 78,453) incorporated by reference herein.

EXAMPLE 1

Reduction of Gel Slugs by Addition of Termamyl or Maxamyl.

5% v/v Terinamyl or Maxamyl solutions (protease free) were prepared in water and used to dissolve photographic bone gelatin. Dissolving was achieved by a cold soak at 4° C. for 30 minutes followed by heating at 50° C. for 45 minutes. The dramatic decrease in gel slugs is illustrated in FIG. 1.

FIG. 1 illustrates that gelatin dissolved under optimum in water at 4° C. for 30 minutes followed by heating at 50° C. for 45 minutes contains approximately 140 gel slugs/g of gelatin in the size range of 54 to 113 microns and greater 30 gel sugs/g of gelatin having a size of greater than 113 microns. Addition of protease free Terinamyl or protease free Maxamyl during gel dissolution reduces the number of gel slugs/g of gelatin in the size range of 54 to 113 microns to approximately 70 and the number of gel slugs/g of gelatin having a size greater than 113 microns to less than 20. This represents nearly a 50 percent decrease in the number of gel slugs.

The invention has been described in detail with particular reference to certain preferred embodiments thereof, but it will be understood that variations and modifications can be effected within the spirit and scope of the invention.

What is claim is:

1. A process for removing gelatin insolubles comprising:

providing a gelatin solution;

adding to the gelatin solution amylase in an amount to provide a concentration of amylase of at least 0.1 ppm for a time sufficient to reduce gelatin insolubles.

2. A composition of matter comprising:

gelatin having a Bloom strength of from 60 to 400 and a concentration of amylase of greater than 0.1 ppm.

3. A process for preparing a gelatin layer that is free of gelatin insolubles comprising:

providing a gelatin solution;

adding to the gelatin solution amylase in an amount to provide a concentration of amylase of at least 0.1 ppm for a time sufficient to reduce gelatin insolubles; and coating the gelatin solution onto a substrate.

4. A photographic product comprising a support, the support coated with the composition of matter described in claim 2.

* * * * *